United States Patent [19]

Rosser

[11] Patent Number: 4,975,218
[45] Date of Patent: Dec. 4, 1990

[54] AQUEOUS SOAP COMPOSITION CONTAINING ETHOXYLATED NONIONIC SURFACTANTS

[75] Inventor: David A. Rosser, Wirral, United Kingdom

[73] Assignee: Chesebrough-Pond's USA Co., Greenwich, Conn.

[21] Appl. No.: 344,339

[22] Filed: Apr. 27, 1989

[30] Foreign Application Priority Data

Apr. 29, 1988 [GB] United Kingdom ............... 8810188

[51] Int. Cl.$^5$ ................ C11D 1/72; C11D 9/18; C11D 9/26
[52] U.S. Cl. .................... 252/117; 252/131; 252/132; 252/DIG. 14; 252/108
[58] Field of Search ....... 252/108, 117, 132, DIG. 14, 252/107, 131

[56] References Cited

U.S. PATENT DOCUMENTS

| | | | |
|---|---|---|---|
| 2,543,744 | 3/1951 | Fox | 252/132 |
| 2,875,153 | 2/1959 | Dalton | 252/132 |
| 2,913,416 | 11/1959 | Fineman et al. | 252/109 |
| 3,218,263 | 11/1965 | Boyle et al. | 252/305 |
| 3,840,465 | 10/1974 | Knowles et al. | 252/90 |
| 3,959,160 | 5/1976 | Horsler et al. | 252/90 |
| 4,285,826 | 8/1981 | Bertozzi et al. | 252/117 |
| 4,397,754 | 8/1983 | Collishaw | 252/91 |
| 4,767,625 | 8/1988 | Mitsuno et al. | 424/95 |
| 4,865,757 | 9/1989 | Singh-Verma et al. | 252/117 |
| 4,897,214 | 1/1990 | Gazzani | 252/170 |

FOREIGN PATENT DOCUMENTS

| | | |
|---|---|---|
| 1154652 | 10/1983 | Canada . |
| 1000300 | 1/1986 | Japan . |
| 1423179 | 1/1976 | United Kingdom . |
| 1487256 | 9/1977 | United Kingdom . |

Primary Examiner—Prince E. Willis
Attorney, Agent, or Firm—Milton L. Honig

[57] ABSTRACT

An aqueous single liquid phase detergent composition suitable for topical application to human skin comprises from 10% to 50% by weight of one or more $C_{12}$ to $C_{18}$ fatty acid soaps; and from 5% to 30% by weight of one or more ethoxylated $C_8$ to $C_{22}$ fatty alcohol having an average of from 20 to 50 ethoxylate groups.

The composition is preferably in the form of a transparent gel product, suitably for washing the face.

10 Claims, 1 Drawing Sheet

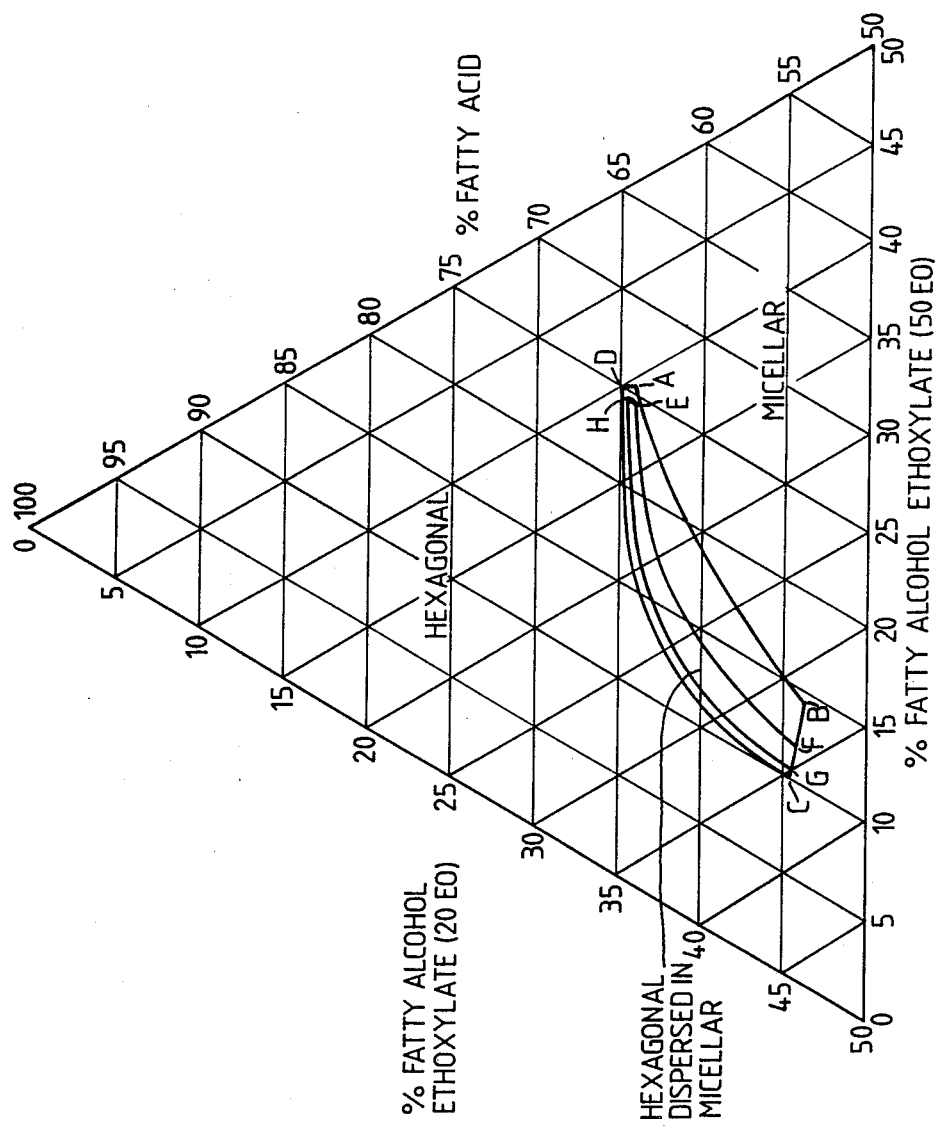

AQUEOUS SOAP COMPOSITION CONTAINING ETHOXYLATED NONIONIC SURFACTANTS

FIELD OF INVENTION

The invention relates to detergent compositions suitable for topical application to human skin or hair, particularly those which are intended for washing the face and other sensitive parts of the body, and which are accordingly characterized by their mildness.

BACKGROUND TO THE INVENTION

The soap component of personal washing products can, in general terms, comprise the soap of medium and/or long chain fatty acids. The soaps of medium chain length fatty acids, such a lauric acid, while being capable of producing a copious foam, can be harsh or aggressive in their reaction to skin, while the soaps of longer chain fatty acids, such as stearic acid, are generally mild, although lacking in their ability to produce adequate foam.

Non-soap detergents, particularly nonionic surfactants can confer mildness to personal washing products, but where rheological stability of such products is of paramount importance, particularly where a gel product is required, then stability problems can arise, such as lowering of viscosity during storage, unless careful attention is given to the choice of nonionic surfactants.

It is known to provide soap-based compositions containing ethoxylated alcohols in aerosol form, which will comprise more than one liquid phase, in contrast to the compositions of the invention which are single phase liquids. GB 1 423 179 (Wilkinson Sword), for example, relates to a pressurized shaving foam which comprises an emulsion of a foamable aqueous concentrate and a liquefied gaseous propellant. The aqueous concentrate may comprise from 2 to 12% by weight of soap and, from 1.5 to 15% by weight of ethoxylated fatty alcohols having 8-60 EO, and a substantial amount of water before emulsification with the propellant liquid.

Addition of low levels of soap to liquid detergents is known to inhibit foam formation. GB 1 487 256 (Henkel) relates to a liquid, lather-regulated washing and cleansing agent comprising a combination of ethoxylated alcohols and from 4 to 6% by weight of $C_{12-18}$ fatty acid soap. Such levels of soap are said to inhibit the undesirable formation of lather in the compositions.

The present invention on the other hand relates to a stable detergent composition for personal washing, comprising a single liquid phase having desired rheological properties and a mild reaction to skin with adequate foaming which can be prepared by careful selection of both fatty acid soaps and ethoxylated fatty alcohols.

DEFINITION OF THE INVENTION

Accordingly, the invention provides an aqueous single liquid phase detergent composition suitable for topical application to human skin comprising:
(i) from 10 to 50% by weight of one or more $C_{12}$ to $C_{18}$ fatty acid soaps, and
(ii) from 5 to 30% of weight of one or more ethoxylated $C_8$ to $C_{22}$ fatty alcohols having an average of from 20 to 50 ethoxylate groups.

DISCLOSURE OF THE INVENTION

THE FATTY ACID SOAP

The composition according to the invention comprises one or more $C_{12}$ to $C_{18}$ fatty acid soaps which can be provided as a preformed ingredient for the composition, but which are preferably formed in situ during the manufacture of the composition by reaction of a fatty acid and an alkali.

The amount of fatty acid soap which is present in the detergent composition according to the invention is from 10 to 50%, preferably from 15 to 40% by weight of the composition.

THE FATTY ACID

The fatty acid from which the soap is formed is chosen from saturated or unsaturated, linear or branched chain fatty acids having from 12 to 18 carbon atoms, or mixtures thereof.

Examples suitable fatty acids include lauric, myristic, palmitic, stearic and oleic acids.

A particularly preferred mixture of fatty acids is lauric acid and myristic acid in a molar ratio of 1:1 to 1:4, ideally from 1:1 to 1:3. Such a blend of fatty acids, when combined with a suitable alkali is capable of maintaining or enhancing clarity in compositions which are required to remain transparent, particularly at storage temperatures of below 10° C., without loss of mildness in its reaction to skin.

A suitable method for measuring the mildness of topically applied products of this nature is described later in this specification.

The amount of fatty acid which is employed in forming the soap is from 5 to 40%, preferably from 10 to 30% by weight of the composition.

Amounts of fatty acid of less than 5% by weight would give rise to a thin product with inadequate detersive properties. Use of greater than 40% by weight fatty acid in forming the soap would give a product having an unacceptably high viscosity.

THE ALKALI

The alkali employed to form the soap is chosen from sodium hydroxide, potassium hydroxide, ammonia and an alkanolamine, or mixtures thereof.

Examples of suitable alkanolamines are monoethanolamine, diethanolamine and triethanolamine.

A particularly preferred alkanolamine is triethanolamine.

The amount of the alkali which is employed in forming the soap ingredients of the detergent compositions according to the invention is that which is normally sufficient to neutralize at least some the free fatty acid present, in order to form the corresponding soap. Accordingly, for some products, it is preferred to employ as little as 80% by weight of the stoichiometric amount required to neutralize all the free fatty acid present, whereas for other products, it is preferred to employ up to 120% by weight of this stoichiometric amount.

In general terms, the amount of alkali employed is from 1 to 30%, preferably from 5 to 25% by weight of the composition.

THE ETHOXYLATED FATTY ALCOHOL

The composition according to the invention also comprises one or more natural or synthetically derived $C_8$ to $C_{22}$ linear or branched chain ethoxylated fatty alcohols having an average of from 20 to 50 ethoxylate groups.

Examples of suitable ethoxylated fatty alcohols are cetyl alcohol ethoxylate (20EO), stearyl alcohol ethoxylate (50EO), and a mixture of these fatty alcohol ethoxylates known as cetostearyl alcohol ethoxylate lauryl alcohol ethoxylate (23EO) and $C_{9-11}$ synthetic alcohol ethoxylate (8EO), such as DOBANOL 91/8.

According to a preferred embodiment of the invention, a mixture of fatty alcohol ethoxylates having different numbers of ethoxylate groups, is employed to give the appropriate phase structure needed to confer a desirable rheological property to the composition according to the invention. Ideally, this phase structure comprises a dispersion of hexagonal liquid crystal droplets dispersed in a micellar "solution".

A particularly preferred combination of ethoxylated fatty alcohols for use in the composition of the invention is the combination of cetyl alcohol ethoxylate 20EO and cetostearyl alcohol ethoxylate 50EO.

The amount of fatty alcohol ethoxylate which is employed in the manufacture of the detergent composition according to the invention is from 5 to 30%, preferably from 8 to 25% by weight of the composition.

THE ACCOMPANYING DIAGRAM

The accompanying diagram shows the structure of preferred compositions according to the invention in terms of soap (expressed as fatty acid) and mixed fatty alcohol ethoxylate ingredients, namely (a) soap (expressed as fatty acid)
(b) fatty alcohol ethoxylate (20EO)
(c) fatty alcohol ethoxylate (50EO).

The sum of (a)+(b)+(c) will accordingly account for 100% of non-aqueous ingredients, or very nearly 100%, if other non-aqueous minor ingredients such as antioxidants, preservatives and perfumes are also present in the composition.

The area on the diagram designated ABCD defines those acceptable compositions according to the invention which are gels of viscosity from 10,000 to 100,000 mPas which are suitable for extrusion from a compressible tube.

The area ABCD defines the composition of the non-aqueous ingredients which have the preferred rheological structure, this being a dispersion of hexagonal liquid crystal droplets dispersed in a micellar "solution".

The most preferred gels are those which fall within the sub area on the diagram designated EFGH; these gels have a viscosity of from 30,000 to 70,000 mPas.

It is to be noted that formulations which fall outside the designated areas towards the top of the diagram are semi-solid hexagonal liquid phase, and those towards the bottom of the diagram are thin liquids which are micellar solutions without any hexagonal liquid phase. These are not gels but are nevertheless structures that fall within the scope of the invention as claimed.

WATER

The detergent composition according to the invention will normally also contain water in an amount of from 20 to 80%, preferably 40 to 70% by weight of the composition.

OPTIONAL INORGANIC THICKENING AGENT

When the composition is a gel, such as one whose non-aqueous ingredients fall within the total designated area indicated in the accompanying diagram, then an inorganic thickening agent is preferably present in order to provide added stability to the product, particularly to prevent phase separation during storage.

Examples of suitable inorganic thickening agents are bentonite, hectorite, magnesium aluminum silicate and sodium magnesium silicate a synthetic complex clay having the generic formula: $[Si_8Mg_{5.1}Li_{0.6}H_{4.6}O_{24}]^{0.6-}Na+_{0.6'}$ an example of which is Laponite, available from Laporte Industries.

The amount of inorganic thickening agent which can optionally be employed in the manufacture of the detergent composition according to the invention is normally from 0.1 to 5%, preferably 0.1 to 1% by weight of the composition.

FURTHER OPTIONAL INGREDIENTS

The composition according to the invention can also contain other optional adjuncts, that is ingredients other than the main ingredients already defined which are conventionally employed in composition for topical application to human skin. These adjuncts, when present, will normally form the balance of the composition.

The composition may optionally include foam improvers such as alkyl sarcosinates, acyl glutamates, alkyl ethanolamides, alkyl amine oxides or alkyl betaines.

Examples of other optional adjuncts include: humectants, such as sorbitol, glycerol, polyethylene glycol (especially PEG 400) and propylene glycol; emollients, such as isopropyl myristate; antibacterial agents, such as Triclosan; natural moisturizing factors, such as lactic acid, pyrrolidone carboxylic acid or urea; UV absorbers; preservatives; and pearlescent agents.

pH

The composition according to the invention will have a pH value of from 6 to 11, preferably from 7 to 9.

PRODUCT FORM AND PACKAGING

The composition according to the invention can be formulated as a liquid, for example as a lotion for use in conjunction with an applicator such a roll-ball applicator, or a container fitted with a pump to dispense the composition, or simply for storage in a non-deformable bottle or a squeezable container.

Alternatively, the composition of the invention can be a solid or semi solid for example a cream or gel for use in conjunction with a suitable applicator or simply for storage in squeezable tube or lidded jar.

Preferably, the composition whether liquid, solid or semi-solid is transparent or translucent.

The invention accordingly also provides a closed container containing a detergent composition as herein defined.

Process For Preparing The Detergent Composition

The invention also provides a process for preparing the detergent composition of the type defined herein, which process comprises the steps of:

(i) preparing a mixture comprising one or more $C_{12}$ to $C_{18}$ fatty acid soaps and one or more ethoxylated $C_8$ to $C_{22}$ fatty alcohols having an average of from 20 to 50 ethoxylate groups, with heating as necessary, and (ii) subsequently packaging the mixture into containers.

A preferred process according to the invention comprises the steps of:

(i) heating a blend of alkali, a premixture of inorganic thickening agent and water, and other water-dispersible ingredients as required, to a temperature of from 70 to 90° C. while maintaining mixing;

(ii) adding to this heated blend, free fatty acid and fatty alcohol ethoxylate as herein defined while maintaining heating and stirring; to form a soap mix, (iii) cooling the soap mix to a temperature not greater than 55° C. and subsequently adding perfume, colorant and preservative as required, and (iv) packaging the detergent composition so obtained into containers.

USE OF THE DETERGENT COMPOSITION

The detergent composition according to the invention is intended primarily as a personal washing product for cleansing the face and other sensitive parts of the body.

It can however, be used for washing the hair as well as the skin. Accordingly, it can also be formulated as a shampoo, a shower gel or liquid or a bath additive.

In use, a small quantity, for example from 1 to 5 ml, of the composition is either rubbed between the hands, together with water to form a foam, which is then applied to the area to be cleansed, or the foam is generated directly on that area. The foam is subsequently rinsed away with clean water.

Determination of Mildness to Skin

The mildness of the detergent composition can be determined by applying it to human skin using a standard protocol and observing the development, if any, of erythema. The test protocol is as follows:

A panel of human volunteers, male or female, is selected on the basis that each has no skin disorders and is not currently taking antihistamines or anti-inflammatory drugs.

The area of skin selected for the test is the anticubital fossa on each arm. Samples of detergent composition are applied to these areas in accordance with the following procedure.

The panelists (up to 32 in total) are instructed to wet (water temperature 32°-34° C.) their left anticubital fossa. A small damp sponge dosed with 0.5 g product is placed in the panellist's right hand, who is instructed to wash his/her left anticubital fossa for exactly 60 seconds (200 strokes in time with a metronome). The anticubital fossa area is then rinsed for 10 seconds and patted dry by the panelists. The wash procedure is repeated on the right anticubital fossa with the appropriate product. The wash procedure is repeated three times daily for 5 consecutive days or a total of 15 washes.

The treatment times are scheduled 90 minutes apart and each test site is evaluated by a trained assessor, immediately prior to each wash and four hours after the third daily wash giving the total of 20 assessments. The evaluations are all carried out under standard lighting conditions using the following grading scheme:

0.5 —barely perceptible erythema
1 —mild spotty erythema/no edema
1.5 —mild/moderate erythema/with or without edema
2 —moderate confluent erythema/with or without edema or vesiculation
2.5 —moderate/deep erythema/edema/vesiculation
3 —deep erythema/edema/vesiculation/weeping.

Each site is treated as described until a grading of "2" or greater is obtained or 15 washings are completed. Any site of a panelist reaching a score of "2" or more following product application is discontinued. The remaining anticubital fossa is washed until a grading "2" or greater is reached or 15 washings are completed which ever comes first.

The cumulative erythema scores for each site for each panelist for the total trial period (20 assessments) are subjected to analysis of variance with panelist, side and product as effects. The cumulative score for discontinued sites is based on carrying forward a score of "2" for each assessment, and hence tends to underestimate the score had treatment been continued.

As a result of this procedure, it will been seen that the lower the score the more mild is the product under test.

EXAMPLES

The invention is further illustrated by the following examples.

Example 1

This example illustrates a clear foamable gel intended for extrusion from a squeezable tube for use in washing the face. The facial washing foamable gel contained the following ingredients:

|  | % w/w |
| --- | --- |
| Lauric acid | 6.7 |
| Myristic acid | 15.6 |
| Triethanolamine (90% aq) | 16.0 |
| Cetyl alcohol ethoxylate (20EO) | 9.6 |
| Cetostearyl alcohol ethoxylate (50EO) | 5.4 |
| Bentonite | 0.2 |
| Preservatives, perfume & colourants | 0.7 |
| Water | to 100 |
| pH | 8.0 |
| Viscosity | 40,000 mPAS* |

*Viscosity was measured using a Brookfield RVT viscometer fitted with spindle B, at 2.5 rpm at 25° C.

Mildness Score

The cumulative mildness score (erythema response) for this product—a total of twenty assessments in accordance with the method described herein—was 7.38.

This was a very low figure i.e. a very mild product, in comparison with a commercially available toilet soap bar which returned a cumulative score of 23.99.

Example 2

This example illustrates a facial washing foam.

|  | % w/w |
| --- | --- |
| Lauric acid | 6.7 |
| Myristic acid | 15.0 |
| Cetyl alcohol ethoxylate 20EO | 9.5 |
| PEG 400 | 5.5 |
| Triethanolamine | 14.5 |
| Hectorite | 0.2 |
| Water | to 100 |
| Perfume, preservatives etc | qv |

Example 3

This example also illustrates a facial washing foam.

|  | % w/w |
| --- | --- |
| Lauric acid | 5.0 |
| Myristic acid | 15.0 |
| Lauryl alcohol ethoxylate 23EO | 12.0 |
| Ceto stearyl alcohol ethoxylate 50EO | 3.0 |
| Triethanolamine | 13.1 |
| Hectorite | 0.2 |

-continued

| | % w/w |
|---|---|
| Water | to 100 |
| Perfume, preservatives etc | qv |

Example 4

This example also illustrates a facial washing foam.

| | % w/w |
|---|---|
| Lauric acid | 5.0 |
| Myristic acid | 15.0 |
| $C_{9-11}$ alcohol ethoxylate 8EO | 8.3 |
| Ceto stearyl alcohol ethoxylate 50EO | 6.7 |
| Triethanolamine | 13.4 |
| Hectorite | 0.2 |
| Water | to 100 |
| Perfume, preservatives etc | qv |

Example 5

This example illustrates a body shampoo for use when showering

| | % w/w |
|---|---|
| Lauric acid | 4.7 |
| Myristic acid | 14.1 |
| Cetyl alcohol ethoxylate 20EO | 14.0 |
| Triethanolamine | 16.9 |
| Sorbitol | 10.0 |
| Water | to 100 |
| Perfume, preservatives etc | qv |

Example 6

This example also illustrates a body shampoo.

| | % w/w |
|---|---|
| Lauric acid | 4.7 |
| Myristic acid | 14.12 |
| Triethanolamine | 16.82 |
| Sorbitol | 5.0 |
| Cetostearyl alcohol ethoxylate 20EO | 8.0 |
| Propylene glycol | 5.0 |
| Laurosyl sarcosine | 3.20 |
| Coconut fatty acid monoethonolamide | 3.00 |
| 2-hydroxy, 4-methoxybenzophenone-5 sulphonic acid | 0.05 |
| Triclosan | 0.1 |
| Water | to 100 |
| Perfume, preservatives etc. | qv |

Example 7

This example also illustrates a facial wash foam.

| | % w/w |
|---|---|
| Myristic acid | 20.00 |
| Stearyl alcohol ethodylate 30EO | 12.00 |
| Ethylene glycol monostearate | 2.00 |
| Behenyl alcohol | 2.00 |
| Triethanolamine | 12.70 |
| Sodium 2 pyrrolidone 5 carboxylate | 0.10 |
| Water | to 100 |
| Perfume, preservative etc. | qv |

I claim:

1. An aqueous single liquid phase detergent composition suitable for topical application to human skin comprising:
   (i) from 10 to 50% by weight of at least one $C_{12}$ to $C_{18}$ fatty acid soap; and
   (ii) from 5 to 30% by weight of at least one ethoxylated $C_8$ to $C_{22}$ fatty alcohol having an average of from 20 to 50 ethoxylate groups;
   which composition comprises a dispersion of hexagonal liquid crystal droplets dispersed in a micellar solution.

2. A composition according to claim 1, in which the soap is derived from the interaction of fatty acid comprising a mixture of lauric and myristic acid, and an alkali.

3. A composition according to claim 2, in which the weight ratio of lauric to myristic acid is from 1:1 to 1:3.

4. A composition according to claim 2, in which the alkali is triethanolamine.

5. A composition according to claim 1, in which the ethoxylated fatty alcohol is selected from the group consisting of cetyl alcohol ethoxylate, stearyl alcohol ethoxylate or mixtures thereof.

6. A composition according to claim 5, in which the ethoxylated fatty alcohol comprises a mixture of cetyl alcohol ethoxylate 20EO and ceto stearyl alcohol ethoxylate 50EO.

7. A composition according to claim 1, which further comprises an inorganic thickening agent is selected from the group consisting of bentonite, hectorite, magnesium aluminium silicate, sodium magnesium silicate and mixtures thereof.

8. A composition according to claim 1, comprising a dispersion of hexagonal liquid crystal droplets dispersed in a micellar solution which falls within the area designated ABCD on the accompanying diagram 9. A composition according to claim 1, which comprises a dispersion of hexagonal liquid crystal droplets dispersed in a micellar solution which falls within the area designated EFGH on the accompanying diagram.

10. A composition according to claim 1, which is a gel having a viscosity of 10,000 to 100,000 mPas.

* * * * *